US005504007A

United States Patent [19]

Haynes

[11] Patent Number: 5,504,007

[45] Date of Patent: Apr. 2, 1996

[54] RAPID THERMAL CYCLE APPARATUS

[75] Inventor: John L. Haynes, Chapel Hill, N.C.

[73] Assignee: Becton, Dickinson and Company, Franklin Lakes, N.J.

[21] Appl. No.: 166,772

[22] Filed: Dec. 14, 1993

Related U.S. Application Data

[63] Continuation-in-part of Ser. No. 770,707, Oct. 3, 1991, abandoned, which is a continuation of Ser. No. 354,172, May 19, 1989, abandoned.

[51] Int. Cl.[6] .............................. C12M 1/40; C12M 1/38

[52] U.S. Cl. .............................. 435/285.1; 435/303.1; 435/305.2; 935/85

[58] Field of Search .............................. 435/3, 91, 288, 435/290, 296, 301, 316, 809; 422/102, 104; 935/85, 88

[56] References Cited

U.S. PATENT DOCUMENTS

| | | | |
|---|---|---|---|
| 3,219,421 | 11/1965 | Schwarz | 422/102 |
| 3,505,023 | 4/1970 | Van Damme | 422/102 |
| 3,556,731 | 1/1971 | Martin | 422/102 |
| 4,256,697 | 3/1981 | Baldwin | 422/102 |
| 4,800,159 | 1/1989 | Mullis et al. | 435/172.3 |
| 4,950,608 | 8/1990 | Kishimoto | 435/290 |

FOREIGN PATENT DOCUMENTS

| | | | |
|---|---|---|---|
| 0200362 | 12/1986 | European Pat. Off. | C12Q 1/68 |
| 4330272 | 11/1992 | Japan | 435/290 |

OTHER PUBLICATIONS

Helge Torgersen, Dieter Blaas and Tim Skern, "Low Cost Apparatus for Primer–Directed DNA Amplification Using Thermus aquaticus–DNA Polymerase", 1989. Analytical Biochem. vol. 176, pp. 33–35.

Royal A. McGraw, Eric K. Steffe and Clyde A. Hutchinson III, "Simple Programmable Apparatus for Enzymatic DNA Amplificationp", 1988. DNA and Protein Eng. Tech. vol. 1, No. (5) pp. 65–67.

Heinz Ulrich Weier and Joe W. Gray, "A Programmable System to Perform the Polymerase Chain Reaction", 1988. DNA. vol. 7. No. (6) pp. 441–447.

*Primary Examiner*—William H. Beisner
*Attorney, Agent, or Firm*—Nanette S. Thomas

[57] ABSTRACT

A thermal cycle apparatus comprises a body having a hollow interior and an access for the passage of liquid into an out of the body. Thermally conductive liquid is contained within the interior of the body. This liquid has a thermal capacity greater than the thermal capacity of the body itself. A pump or piston is provided for moving liquid into and out of the body in conjunction with the access opening. The liquid within the body is alternated between lower and higher temperatures in repeating cycles. A well or container for holding a sample of material to be subjected to cyclic thermal changes is held in contact with the liquid within the body in order to conduct the cyclic temperature changes of the liquid to the sample. A method for thermally cycling samples of material between lower and higher temperatures is also within the purview of the present invention.

1 Claim, 8 Drawing Sheets

RAPID THERMAL CYCLE APPARATUS

This application is a continuation-in-part of patent application Ser. No. 07/770,707, filed Oct. 3, 1991, now abandoned, which is a continuation of patent application Ser. No. 07/354,172, filed May 19, 1989, now abandoned.

BACKGROUND OF THE INVENTION

1. Field of the Invention

The present invention relates to a thermal cycle apparatus, and more particularly relates to such an apparatus useful for the amplification of nucleic acid sequences, and further relates to a method for thermally cycling samples of material, such as nucleic acid sequences, between lower and higher temperatures in order to amplify the amounts of such materials to facilitate their detection.

2. Background Information

Genetic diseases or disorders, infectious diseases and related disorders may be diagnosed by analyzing targeted nucleic acid sequences in DNA (deoxyribonucleic acid) or RNA (ribonucleic acid). These nucleic acid sequences of interest generally are small segments of the DNA or RNA strands. In performing this analysis for diagnosis of a disease or a genetic disorder, it is appreciated that extremely small amounts of genetic material are all that is available.

For detecting the presence of certain sequences of nucleic acids, a relatively new procedure has been developed which amplifies the targeted sequence. This process is known as polymerase chain reaction (PCR) and was described by Saiki et al., Science 230, 1350–1354 (1985) European Patent Application No. 86 302298.4, published Dec. 10, 1986, and U.S. Pat. No. 4,800,159. In addition to increasing the amounts of DNA or RNA material in order to make nucleic acid sequence more easily detectable, the PCR process enhances the sensitivity of the detection of genetic disorders. For example, by amplifying the targeted nucleic acid sequence, it is possible to study single base changes, analyze the absence of base pairs and determine whether there may be translocations of the nucleic acids within the specific sequence of interest. While PCR is an excellent technique for amplifying nucleic acid sequences, there are other procedures which have been used to provide such amplification.

Briefly, PCR involves a primer-mediated enzymatic amplification of the nucleic acid sequence. For example, to amplify specific DNA segments, the DNA is denatured with a pair of synthetic oligonucleotides which serve as primers for annealing with the single strands of denatured genomic DNA. The synthetic oligonucleotides are then extended with a DNA polymerase and deoxynucleotide triphosphates in order to double the number of nucleic acid sequences between the primers. With repeated cycles of denaturation, primer annealing and extension of the primers, the base pair region between the primers is copied over and over again, resulting in an exponential amplification of the DNA segment of interest. The details of the PCR process are found in the aforementioned publications.

A thermally stable DNA polymerase from *thermus aquaticus* (Taq) has become available, and when used in PCR, significantly simplifies the reaction, as reported by Weier et al. in *DNA*, vol. 7, no. 6, 1988. The PCR reaction is significantly simplified because amplification is achieved by repeatedly heating and cooling of samples containing the thermally stable polymerase (Taq), the primers, genetic material to be amplified and the deoxynucleotide triphosphates. According to Weier et al., the Taq polymerase has maximum activity between 60° C. and 85° C., and is not destroyed when heated to 95° C. for several minutes. Since denaturation of the genetic material, DNA, can be accomplished at temperatures in the 91°–93° C. range, the Taq polymerase is not destroyed at these temperatures.

Primer annealing is achieved by cooling the sample of materials, so that there is a rapid change of temperature, from hot to cold, of the genetic materials to be amplified. Repeatedly heating and cooling of samples of genetic material, along with the other ingredients for PCR, require proper equipment, such as a thermal cycle apparatus.

It is often desirable when amplifying DNA segments of interest, in conjunction with selected enzymes such as DNA polymerase, to run through perhaps 15–20 rapid heating/cooling cycles. Present performance is limited by the speed at which available equipment may cycle between the temperature extremes. For example, there is a PCR apparatus marketed by Perkin Elmer Cetus, known as a DNA thermal cycler. In this and other similar cycling systems, small tubes or microtiter trays are loaded onto a metal heating/cooling block which is designed to provide equalized temperatures. Heating is achieved by electric heaters embedded in the heat block; cooling is done either by circulating cool water or by a thermal electric cooler. Heat transfer rates of the existing cycling equipment are limited to thermal changes of less than 1° C./sec.

Such limited speed is attributed to at least two factors. First, the energy delivered to the system must heat or cool the large mass of the heat block, heating rods, and cooling water, before the metal block transfers heat to the sample undergoing amplification. Second, thermal contact between the sample and the heat block usually is poor. Heat must pass through a relatively thick-walled plastic tube, which holds the material to be amplified, which in turn is in relatively loose contact with the heat block.

As a result of the designs of the existing thermal cycling systems, the efficiency of performance and operation is quite low. The combined thermal mass of the heat block, the heater rods and the cooling water exceeds the thermal mass of the sample liquid to be cooled generally by a factor of thirty or more. This means that less than 3% of the energy is used to heat or cool the sample, while the rest of the energy is wasted. Since all of the heat energy delivered to the system must be removed by the cooling water, the cooling apparatus grows way out of proportion to the relatively small samples of material undergoing PCR.

Another apparatus which suffers from the same deficiencies as pointed out above, is described by N. S. Fouikes et al., in *Nucleic Acids Research*, vol. 16, no. 12, 1988. Other apparatuses for DNA amplification are described by Torgersen et al., in *Analytical Biochemistry*, 176, 33–35 (1988) and by McGraw et al., in *DNA and Protein Engineering Techniques*, vol. 1 no. 5, 65–67 (1988).

Rather than use an automated thermal cycle apparatus for PCR, it is known that racks of tubes containing the sample materials have been moved from a cold bath to a hot bath in repeating cycles. This type of arrangement is cumbersome, requires substantially more user attention and has many of the same inefficiencies as the previously described existing equipment.

Improvements are thus required in a thermal cycle apparatus for rapid heating/cooling cycles useful for the amplification of nucleic acid sequences, such as employed in the PCR process. The present invention is directed to such an improved rapid thermal cycle apparatus, the device use therein and methods of use.

SUMMARY OF THE INVENTION

The thermal cycle apparatus of the present invention comprises a body having a hollow interior, and access means for the passage of liquid into and out of the body. Thermally conductive liquid is within the interior of the body, this liquid having a thermal capacity greater than the thermal capacity of the body. Means are provided for moving the liquid into and out of the body in conjunction with the access means so that liquid in the body alternates between lower and higher temperatures in repeating cycles. Also included are means for holding a sample of material to be subjected to cyclic thermal changes. This holding means is in contact with the liquid in order to facilitate conduction of the cyclic temperature changes of the liquid to the sample.

In a preferred embodiment of the invention, a thermal cycle apparatus useful for the amplification of nucleic acid sequences comprises a body having a hollow interior and liquid passage ports. A thermally conductive liquid is within the interior of the body. A plurality of wells, for holding samples of nucleic acid sequences, depends into the interior of the body and is immersed in the liquid. Pistons or pumps are associated with the liquid passage ports for moving the thermally conductive liquid having alternating lower and higher temperatures into and out of the interior of the body in repeating cycles. Thus, the samples in the wells are subjected to rapid cyclic thermal changes.

Another aspect of the present invention is a thermal cycle device for use in the amplification of nucleic acid sequences comprising a body having a hollow interior. Access means are provided for the passage of liquid into and out of the body. Means are provided for holding a sample of material to be amplified by being subjected to cyclic thermal changes. The body has a relatively low mass compared to the liquid to be introduced into the body, so that changes of liquid temperature inside the body cause the body rapidly to change its temperature for efficient thermal cycling of the sample held in the body.

A further aspect of the present invention is a method for thermally cycling a sample of material between lower and higher temperatures. This method involves placing a sample of material to be thermally cycled into a carrier which is a component of a body with a hollow interior. Liquid is introduced into the interior of the body so that the liquid has a greater thermal mass than the body. This liquid is caused to come in contact with the carrier. The method further includes cycling the temperature of liquid in the body by alternately introducing to and removing from the body liquid of lower and higher temperature in order to subject the sample to rapid cyclic thermal changes.

In a preferred embodiment of this aspect of the invention, the method for thermally cycling samples of material between lower and higher temperatures comprises placing samples to be thermally cycled into a plurality of wells. These wells are contained in a body with a hollow interior and are positioned so that the wells depend into the interior. Liquid is introduced at a first temperature into the interior of the body, with the wells being immersed in the liquid. The method then involves removing the liquid of the first temperature from the body and introducing liquid at a second temperature, substantially higher or lower than the first temperature, into the interior of the body, again so that the wells are immersed therein. Introduction and removal of liquids of different temperatures are repeated in cycles in order to subject the samples in the wells to rapid cyclic thermal changes.

In accordance with the principles of the present invention, a rapid thermal cycle apparatus is provided which is particularly suitable for the amplification of nucleic acid sequences. As mentioned above, the thermal cycle device, used in the apparatus, and the method for using same are all within the purview of the present invention. It is believed that the thermal cycle apparatus hereof will permit rapid heating/cooling cycles to be carried out many times faster than existing apparatus used for nucleic acid sequence amplification. The design of the present apparatus renders it substantially more efficient than previous thermal cycle apparatuses, which should result in a smaller, lower cost system.

For example, the body of the thermal cycle apparatus herein may be made out of plastic which would not only permit the cost to be low, but could also make the device disposable. If the body of the thermal cycle apparatus is made of plastic, the samples to be amplified could be placed directly in the body, rather than first in conventional test tubes. This arrangement would eliminate a variable which would affect response time, i.e., the relatively poor thermal contact between the heat block and the sample vessel (test tube). Further, the body of the thermal cycle apparatus could be designed to have relatively thin walls, thereby further reducing the thermal resistance between the sample of materials and the heat transfer liquid inside the body. In use, the present invention permits rapid temperature changes in the samples of materials, at least in the order of 1.0° C./sec. Other advantages and features of the present invention will become more apparent upon reading the Detailed Description below.

DETAILED DESCRIPTION

Figure 1:
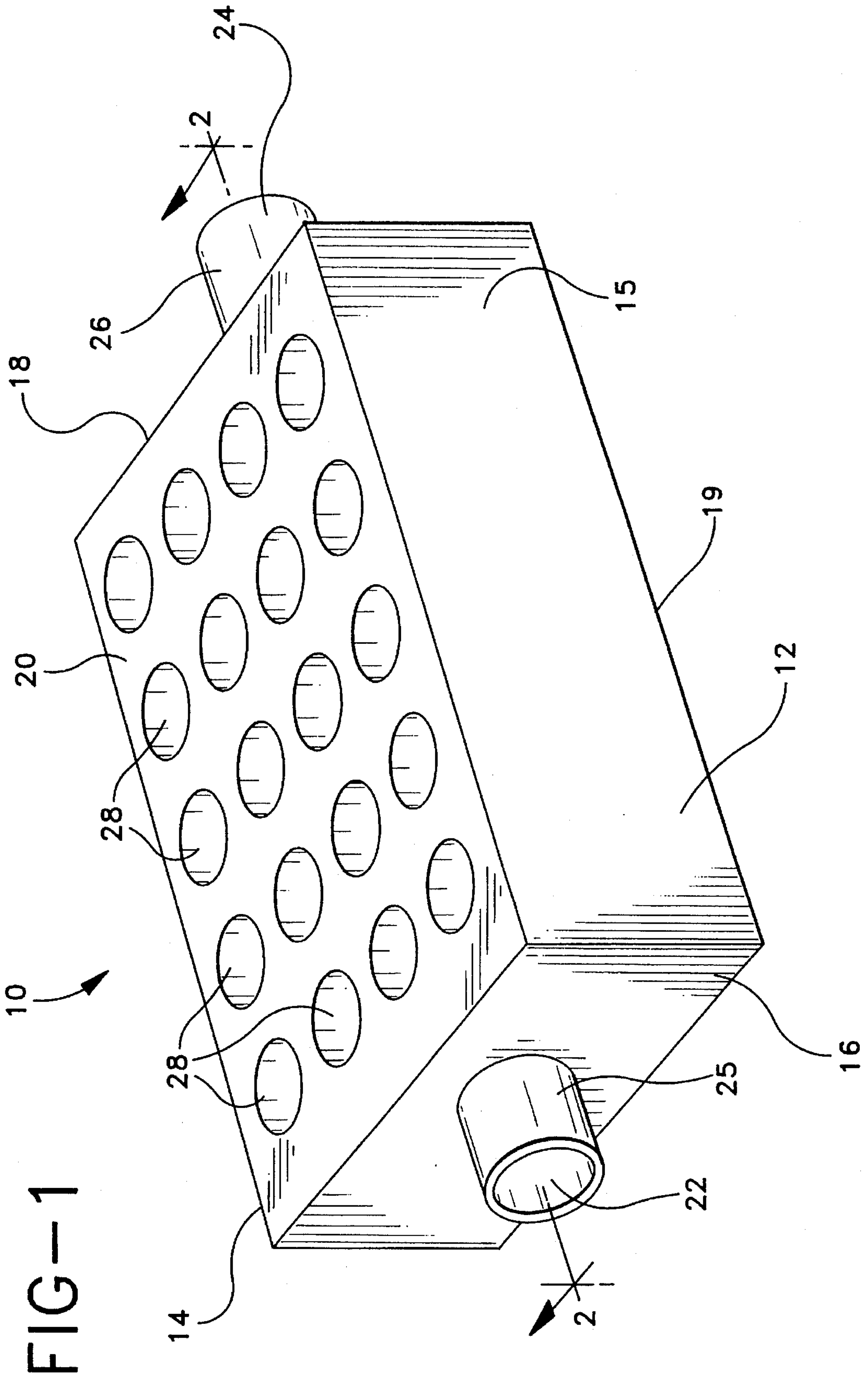
FIG. 1 is a perspective view of a preferred embodiment of the rapid thermal cycle device of the present invention for use in the amplification of nucleic acid sequences.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

Figure 2:
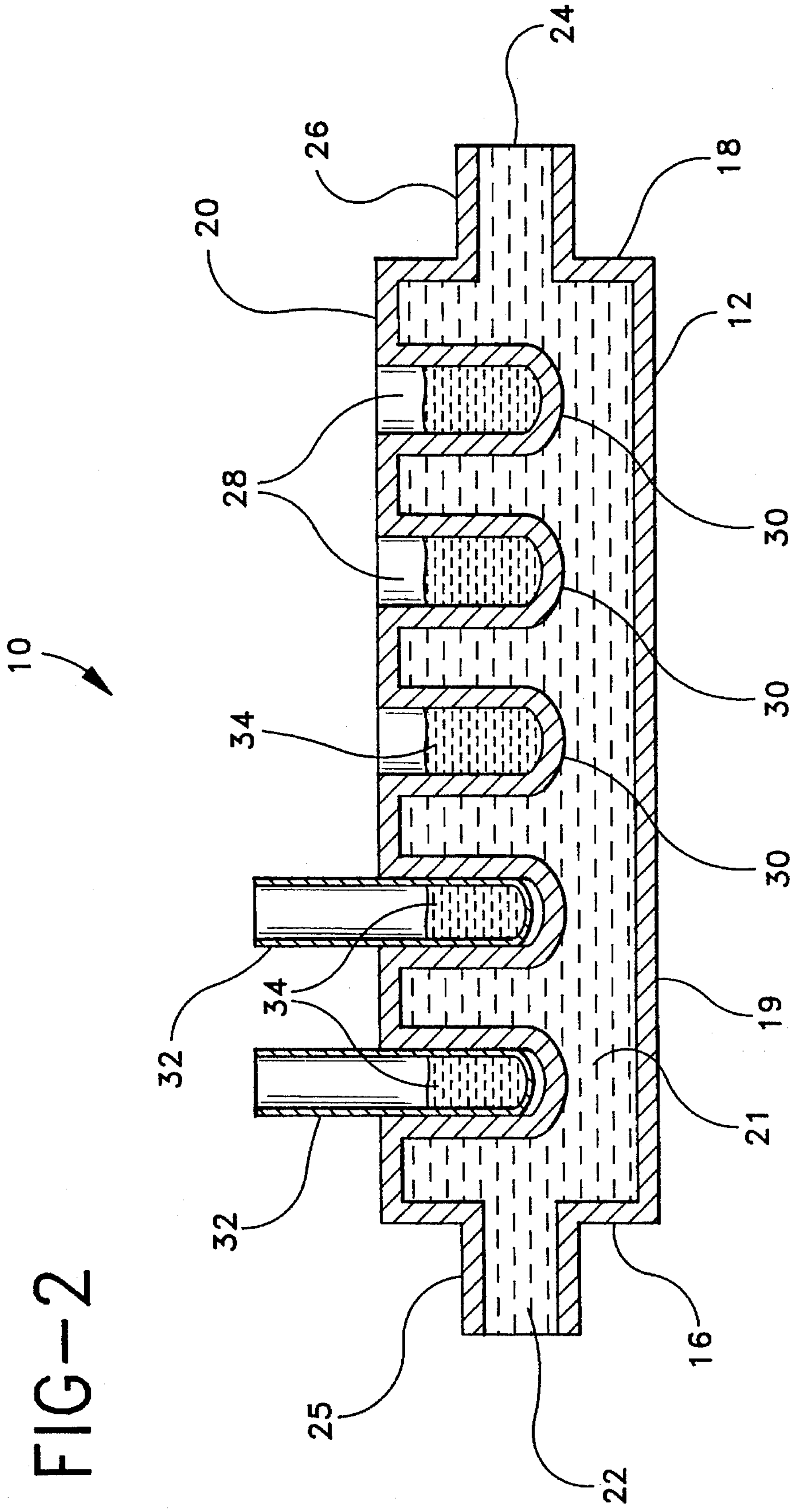
FIG. 2 is a cross-section of the device of FIG. 1 taken along line 2—2 thereof, illustrating different techniques for holding samples of materials to be amplified.

Adverting now to the drawings, and FIG. 1 in particular, there is illustrated a preferred embodiment of a rapid thermal cycle device 10, which is useful for the amplification of nucleic acid sequences. This device has a body 12 which is preferably a hollow block of material. Although body 12 may be formed in any suitable and practical shape, in the embodiment being described it is preferably box-shaped with a pair of sidewalls 14 and 15, a pair of endwalls 16 and 18, and a substantially flat lower surface 19 and a substantially flat upper surface 20. These outer walls and surfaces of body 12 enclose the hollow interior 21 of the body, as seen in FIG. 2, taken in conjunction with FIG. 1. Interior 21 is completely enclosed, except for liquid passage port 22 which passes through end wall 16 of the body and liquid passage port 24 which passes through endwall 18 of the body. In this particular embodiment, there are two liquid passage ports, but the present invention is not limited to two since the number of ports may vary, higher or lower, depending upon the design and configuration of the body. It can be seen that liquid passage port 22 extends through a short tube 24 protruding from endwall 16, and similarly, liquid passage port 24 extends through a short tube 26 protruding from the opposite endwall 18 of the body. These liquid passage ports provide communication between interior 21 of the body and the outside environment, so that liquid may be moved into and out of the body, according to the principles of the present invention.

Formed in upper surface 20 of the body is a plurality of wells 28, which depend downwardly (in the orientation illustrated in FIG. 2) into interior 21 of the body. Wells 28 preferably are relatively elongate, cylindrically shaped receptacles configured to receive conventionally-shaped test tubes. It is also preferred that wells 28 include sidewalls 30 which are integrally formed in, and from the same material as, the upper surface of the block of material forming body 12. In such case, upper surface 20 with integrally constructed wells 28 may be molded in a single step, leading to easy fabrication of this part of the thermal cycle device.

In order to realize the benefits of the present invention, it is preferred that the walls of the body, including sidewalls 14 and 15, endwalls 16 and 18, lower surface 19, upper surface 20 and sidewalls 30 of wells 28, be relatively thin in dimension in order to provide a body with low thermal mass. The most straightforward, but not necessarily limitative, construction of body 12 is one in which all of the walls are of the same relative thickness, such as seen more clearly in FIG. 2. In this arrangement, manufacture of the block of material forming body 12 is straightforward and convenient. For purposes of the present invention, all of the aforementioned walls may have a thickness between about 0.002 and 0.125 inches (0.051 and 3.175 mm), and preferably having a thickness between about 0.004 and 0.020 inches (0.102 and 0.508 mm).

Figure 3:
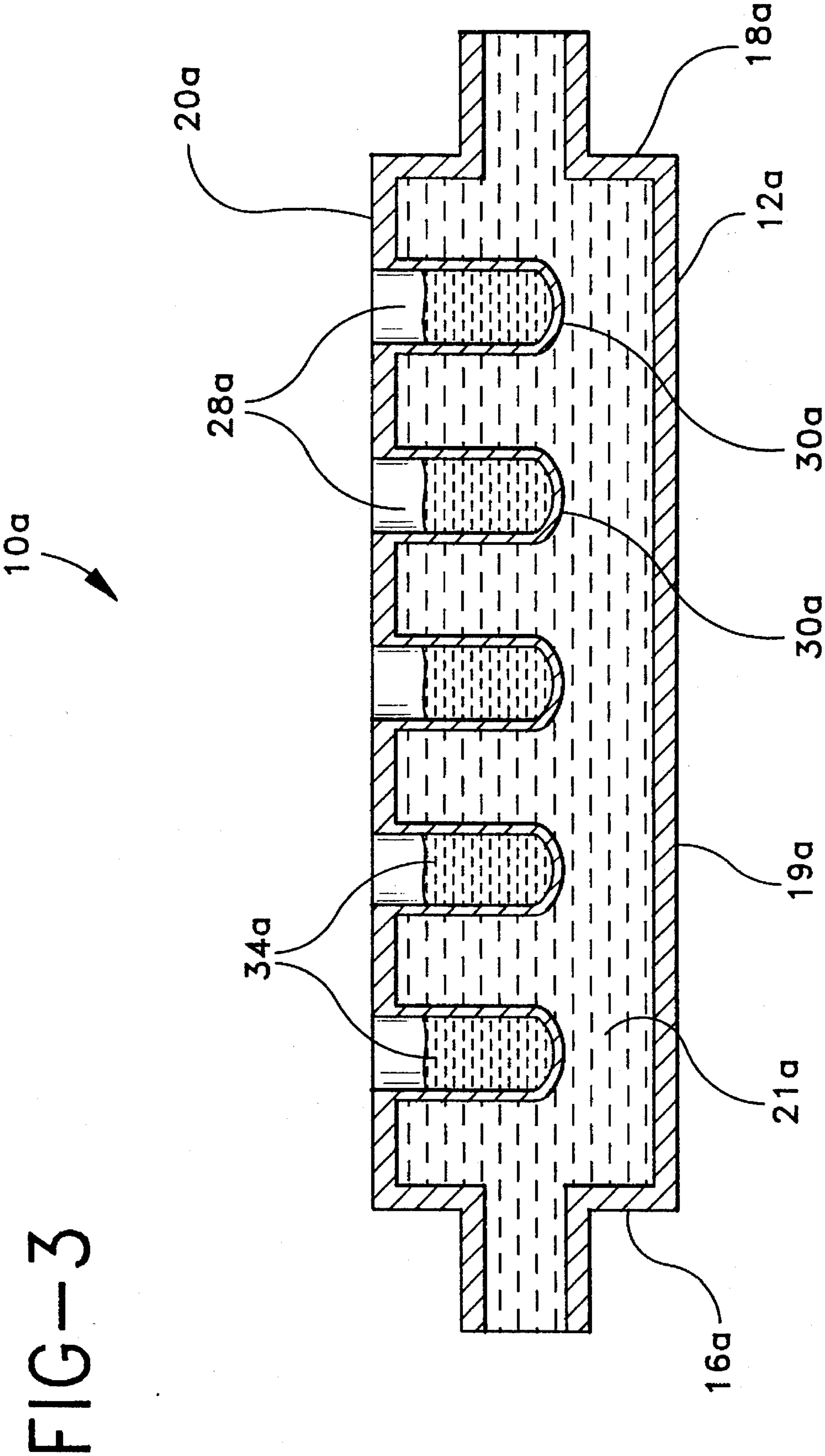
FIG. 3 is a cross-section of a device, similar to the device of FIG. 1, but having wells of reduced wall-thickness for improved thermal conductivity between the liquid in the body and the samples of materials in the wells.

There are variations of wall thicknesses which fall within the purview of this invention. For example, an alternative construction of the wells is illustrated in FIG. 3. Although the thickness of the sidewalls, endwalls **16*a* and 18*a*, lower surface 19*a* and upper surface 20*a* are all substantially the same, and also similar in thickness to the embodiment of FIG. 2, the thickness of sidewalls 30*a* of the wells 28*a* is different. It can be seen that sidewalls 30*a* have a substantially reduced thickness than the comparable sidewalls of the wells in the previously described embodiment of FIG. 2. This reduced thickness of sidewalls 30*a* facilitates the conduction of heat thereacross. In this alternative embodiment, sidewalls 30*a* are readily formed, and preferably vacuum molded, so that the thickness may be as thin as practical while still maintaining the integrity of the receptacles which depend into interior 21*a*. In this embodiment, sidewalls 30*a*** may have a thickness between about 0.002 and 0.030 inches (0.051 and 0.762 mm).

Referring now to the embodiment of. FIG. 2, it can be seen that wells 28 are preferably configured to receive conventionally-shaped test tubes 32. These test tubes serve as carriers or vessels into which samples of compositions to be thermally cycled are placed. These compositions are usually in liquid form and contain the nucleic acid sequences which are to be amplified and subsequently detected, preferably using the PCR technique. As seen in FIG. 2, test tubes 32 with samples 34 are received within wells 28, with the test tubes preferably being held in relatively tight contact with sidewalls 30 of the wells, to facilitate optimum conduction of heat into and out of the test tubes.

Alternatively, whether using the embodiment of FIG. 2 or FIG. 3, the samples containing the nucleic acid sequences of interest may be placed directly into the wells. Inasmuch as device 10 may be fabricated inexpensively so that it may be disposable after single use, direct placement of sample compositions 34 or **34*a*** into the wells is an alternative which the user may choose.

Whether using test tubes to hold the samples to be amplified, or placing the samples directly into the wells, it can be seen that samples 34 (or **34*a*) are maintained well within interior 21 (or 21*a*) of the body of this device. When a thermally conductive liquid is introduced into the interior of the body, there is intimate contact between this thermally conductive liquid and wells 30 so that the wells are substantially immersed in the liquid. As mentioned earlier, passage ports 22 and 24** are available so that this thermally conductive liquid, such as water or the like, may be moved into and out of the interior of the body, as will be explained in greater detail hereinafter. The intimate contact between the thermally conductive liquid within the interior of the body and the wells, holding the sample of compositions to be amplified, greatly facilitates the conduction of heat into and out of the wells, depending upon the temperature of the thermally conductive liquid which is within the body of the device at any particular time.

Figure 4:
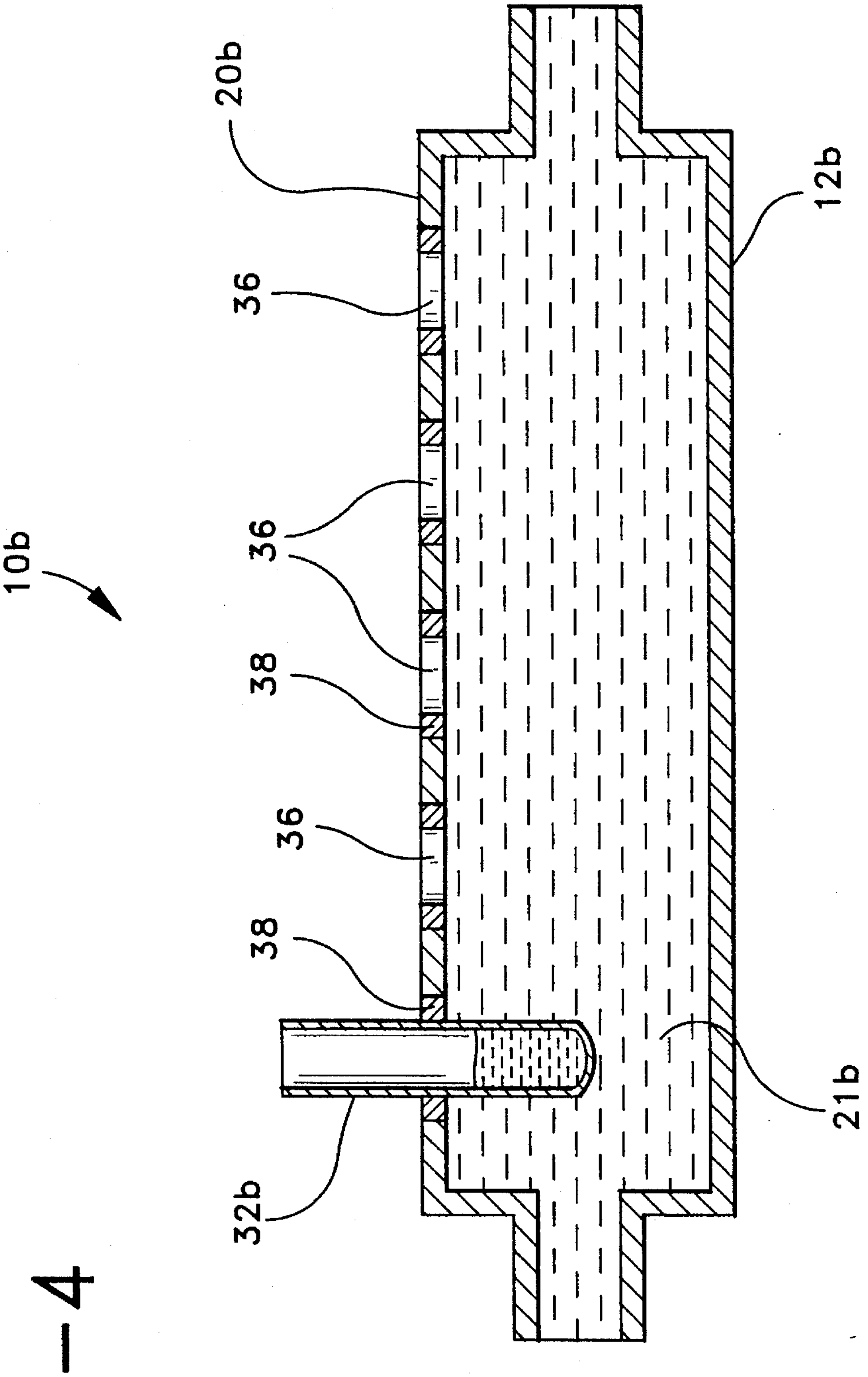
FIG. 4 is a cross-sectional view of an alternative construction of the rapid thermal cycle device of the present invention permitting removable wells for holding samples of materials.

While the embodiments of FIGS. 1–3 envision the wells being permanently fabricated in the body so that the wells depend into the interior thereof, still other alternative constructions fall within the purview of the present invention. One such other alternative is illustrated in FIG. 4. In this alternative, body **12*b* includes an upper surface 20*b* which is substantially similar in thickness to the upper surfaces of the previously described embodiments. However, rather than having wells already formed together with the upper surface, there are no integrally formed wells in this embodiment. Instead, there are a plurality of holes 36 through upper surface 20*b*. Each hole 36 is preferably circular in shape and includes a circular gasket or grommet 38. These gaskets have an inside diameter which will provide an interference fit with the diameter of standard size, conventional test tubes. When the test tubes, with samples of materials to be amplified, are inserted through holes 36, in order to depend into the interior 21*b* of body 12*b*, gasket 38 provides a liquid-tight seal against the outer surface of the test tube. Then, when liquid is introduced into interior 21*b* of the body, the liquid-tight seal between gaskets 38 and test tubes 32***b* prevent liquid from escaping from the interior of the body. In this embodiment, test tubes 32*b* are directly, but removably, immersed within the thermally conductive liquid which is introduced into interior 21*b* of the body. It is appreciated that other variations of the rapid thermal cycle device are contemplated by the present invention.

Although the embodiments described herein illustrate 20 wells, or provisions therefore, carried by the thermal cycle device, this number may vary up or down. With respect to the materials out of which body 12 may be fabricated, it is preferred that the material be plastic, such as polypropylene or polycarbonate or the like, so that the body may be molded in an inexpensive fashion. Further, if a low-cost rapid thermal cycle device is manufactured, it may also be disposable after single use. However, it is also possible to make the device out of metal, such as stainless steel, ceramic, glass or combinations of any of the foregoing materials. Ideally, the material would be chosen to provide a device with low thermal mass or capacity while striving for good heat transfer particularly in the area of sidewalls 30 of wells 28.

With respect to the size and volume of body 12, the thermally conductive liquid to be used in the thermal cycle procedure should be taken into account. Insofar as it is the purpose of the present invention to provide substantially better heat transfer capabilities, the mass of the liquid which is introduced into the hollow block should be greater than the mass of the hollow block itself. Further, the choice of materials of the hollow block, as well as its size and volume, should permit the thermally conductive liquid, when introduced into the block, to have a thermal capacity greater than the thermal capacity of the hollow block itself. As a result, when high temperature liquid within the block is replaced with cold liquid in the block, rapid changes of temperature are experienced in the block itself because of the aforementioned mass and thermal capacity differences between the block of material and the thermally conductive liquid. These rapid temperature changes produce a change in the samples of nucleic acid sequences of at least 1° C./sec and even higher.

Figure 5:
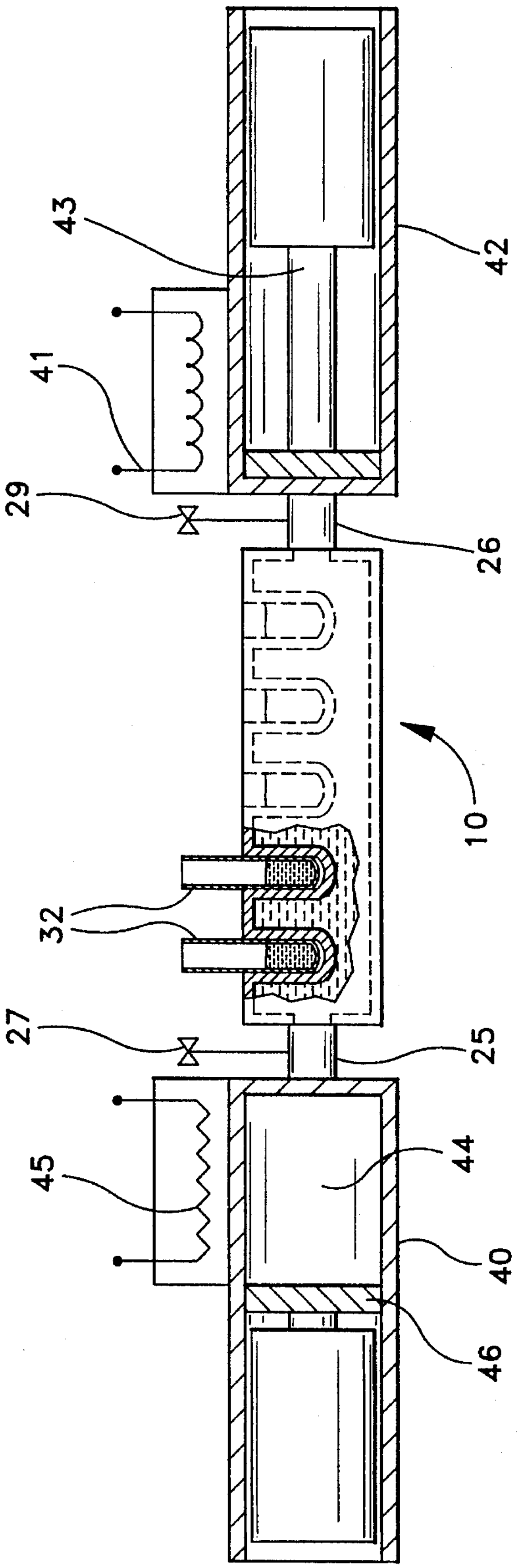
FIG. 5 is schematic sectional view of one embodiment of the rapid thermal cycle apparatus of the present invention with pistons for transferring liquid into and out of the cycle device.
Figure 6:
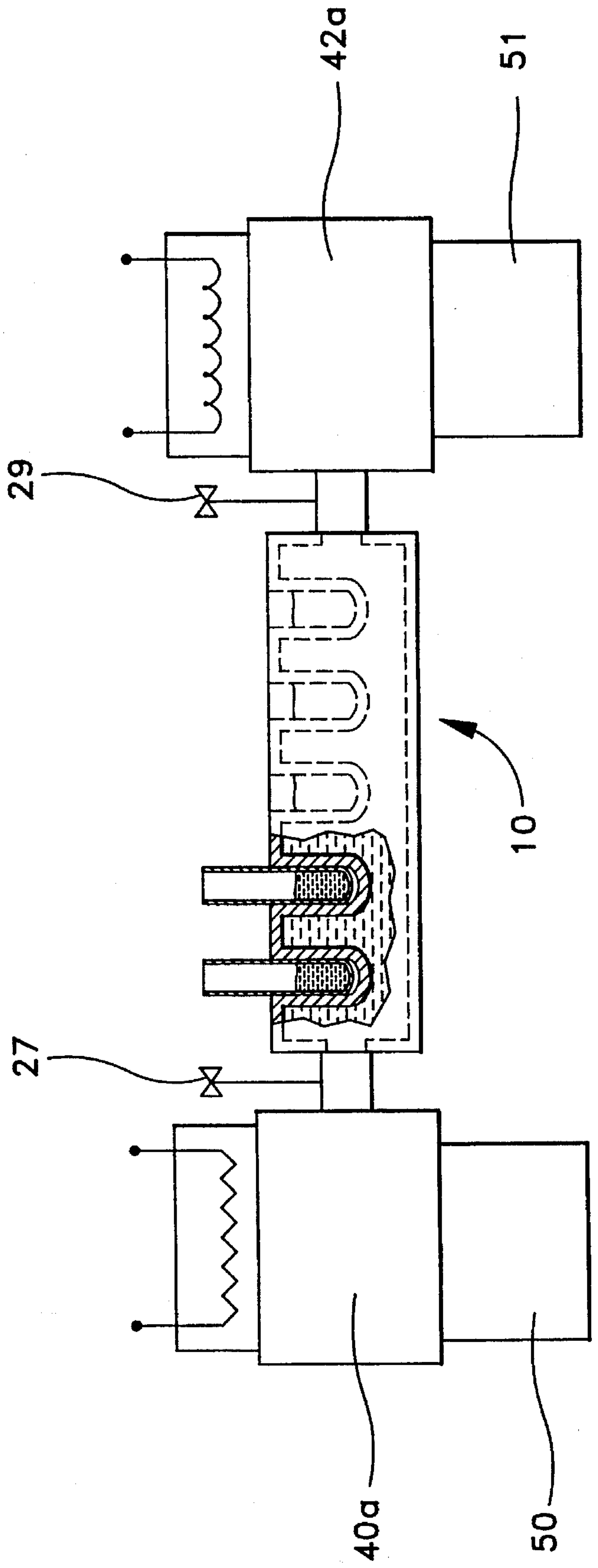
FIG. 6 is a schematic sectional view of another embodiment of the rapid thermal cycle apparatus of the present invention with pumps for transferring liquid into and out of the cycle device.
Figure 7:
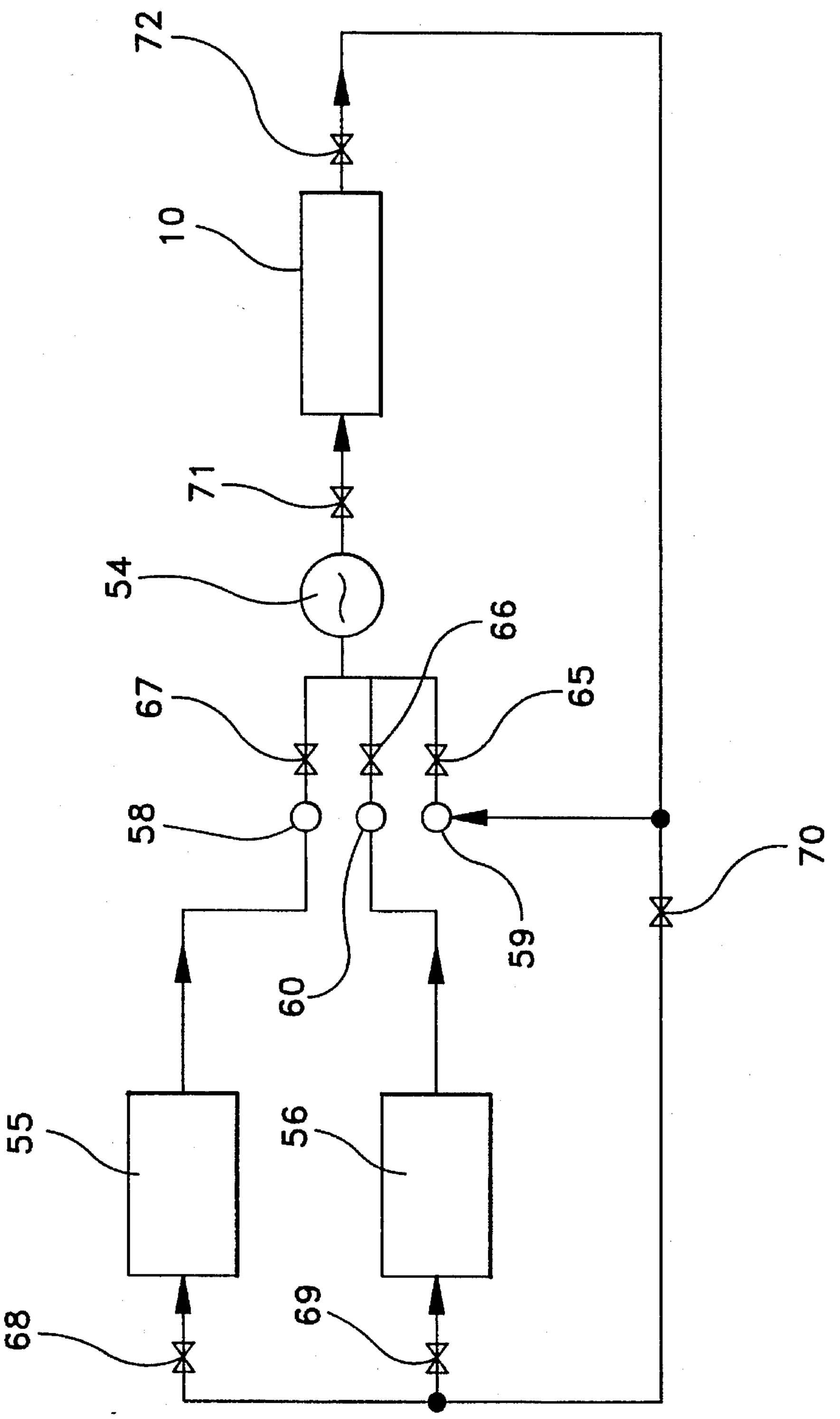
FIG. 7 is schematic plan view of still another embodiment of the rapid thermal cycle apparatus of the present invention with pumps for transferring liquid into and out of the cycle device.

There are a number of ways to move the thermally conductive liquid into and out of body 12. Some of these techniques are illustrated in FIGS. 5, 6 and 7. Turning first to FIG. 5, rapid thermal cycle device 10 is interposed between a hot liquid tank 40 and a cold liquid tank 42. Hot liquid tank is in fluid communication with device 10 by virtue of a connection with short extension 25 and valve 27, whereas cold liquid tank 42 is in fluid communication with device 10 by virtue of a connection with short extension 26 and valve 29 on the other endwall of the device.

Liquid 44 within tank 40 is heated by a heating element 45, so that the temperature of liquid 44, preferably water, may be heated to an elevated temperature, perhaps up to or in excess of 95° C. While liquid 44 is within tank 40 in order to be heated, a piston 46 is retracted within tank 40.

While the liquid in the hot liquid tank is being heated, cool liquid is within, and substantially fills the interior of device 10. This cool liquid has been introduced into device 10 through passage port 26 and open valve 29 which is in fluid communication with cold liquid tank 42. It can be seen that there is a piston 48 inside cold liquid tank 48 which is extended in order to compress the space within the tank and force cold liquid out of the tank and into device 10. Prior to being forced out of the cold liquid tank, liquid therein is cooled by virtue of cooling coils 49, which employs well-known refrigerants in order to provide temperatures as cool as 37° C. or lower.

Pistons 46 and 48 in the respective hot and cold liquid tanks are coordinated so that when piston 46 is retracted, piston 48 is extended. Valves 27 and 29 are also coordinated so that when valve 27 is closed, valve 29 is opened. In this arrangement, cold liquid from tank 42 is delivered into the interior of cycling device 10, and the liquid which was within the interior is emptied, through port 25, into hot liquid tank 40 because piston 46 retracts. When it is time to cycle, piston 46 extends to compress the space within the hot liquid tank, while at the same time piston 48 retracts to open up the liquid space within cold tank 42. As a result, liquid within the interior of device 10 then empties into the cold liquid tank. Once the tank is emptied, hot liquid fills the interior of the device. This liquid flow alternates so that there is alternating delivery of liquids from the hot and cold liquid tanks to the interior of the cycling device in repeating cycles. The use of valves 27 and 29 facilities separation of the liquids. Most preferably, valves 27 and 29 are operated by a control system dependent on time and temperature. The respective forward and rearward strokes of the respective pistons in the hot and cold liquid tank causes the liquid to flow first in one direction into the body of the cycling device and then in the opposite direction out of the device so that the interior of the body will have liquid of alternating higher and lower temperatures.

In FIG. 6, the operation of the thermal cycle apparatus is substantially the same as the apparatus of FIG. 5. However, instead of pistons, hot liquid tank 40*a* has a first pump 50 associated therewith, and cold liquid tank 42*a* has its own pump 51 associated therewith. In this embodiment, liquid from hot tank 40*a* is delivered, by virtue of pump 50 operation, into the interior of device 10, while at the same time, liquid which was within the device is emptied into cold liquid tank 42*a*. Upon cycling, pump 51 operates in order to reverse the direction of liquid flow into device 10, thereby causing cold liquid from tank 42*a* to be introduced into the device, while liquid which was in the interior of device 10 then empties into hot liquid tank 40*a* to be reheated.

It is also feasible to include a pump which would circulate the liquid within the interior of device 10 to assure efficient heat transfer between the liquid within the device and the sample materials which are to be subjected to thermal cycling. In this arrangement, the circulating liquid provides a greater efficiency of heat transfer thereby allowing use of a lower thermal mass of liquid to achieve the desired results. Accordingly, any desired intermediate temperature could be achieved by a trimming of the positions of either the pistons or delivery pumps, and hot or cold liquid may be added as required, under control or a sensor in thermal contact in the cycling device.

Another variation on the delivery of thermally conductive liquid to and from cycling device 10 is schematically illustrated in FIG. 7. In this embodiment, there is one pump 54 which moves liquid in one direction into and out of cycling device 10. Liquid is heated in hot liquid tank 55, and liquid is cooled in cold liquid tank 56. Pump 54 may be selectively positioned to accept hot liquid from tank 55 by connection to hot liquid outlet 58. Thus, when it is appropriate to cycle hot liquid into device 10, pump 54 is selectively connected to outlet 58 whereupon hot liquid flows from tank 55 through appropriate piping, and then into the interior of device 10. When hot liquid is being so delivered, the liquid within the interior of the device 10 passes out of the opposite liquid passage port whereupon it returns the hot liquid tank in order to be reheated. As an alternative path, liquid from device 10 may be emptied into a holding area 59 in order to maintain the temperature at some intermediate level. The liquid is then recirculated from this intermediate area to and from the device.

When it is appropriate to cycle cold liquid into cycling device 10, pump 54 is place in selective engagement with cold liquid tank 56 by making connection with liquid tank 56 by making connection with liquid connector 60. This is accomplished with various valves 65, 66, 67, 68, 69, 70, 71 and 72 that are distributed throughout the system. Thus, cold liquid from tank 56 is pumped into cycling device 10, while the liquid which was inside of device 10 is emptied and returned to cold liquid tank 56, or alternatively to area 59 when some intermediate temperature is desired. It is also feasible to mix liquid from hot tank 55 and from cold tank 56 when delivering liquid to device 10.

There are, of course, other ways contemplated by the present invention for moving hot and cold liquids, in cyclic fashion, into and out of cycling device 10 for purposes of the present invention.

Although not specifically illustrated in the drawings, it is contemplated that the rapid thermal cycle apparatus herein would include, as appropriate, control mechanisms, such as sensors and the like, for regulating and monitoring the temperatures of liquid in the respective liquid tanks, as well as in the cycling device itself. Further, appropriate valves, tubing or piping and liquid flow control mechanisms, well within the knowledge of those skilled in the art, may be included for assuring the adequate movement of liquid into and out of cycling device. In addition, timing mechanisms, electronic or otherwise, may be included for maintaining time intervals for each of the hot and cold temperature cycles, and for counting the number of repetitions which might be used for such procedures as polymerase chain reaction. Many of these standard elements, such as valving, tubing and timing mechanisms -may be similar to those described in the aforementioned Weier et al. publication.

While the present thermal cycle apparatus is useful for the amplification of nucleic acid sequences, it is particularly suitable for amplifying DNA segments. Samples of DNA segments or sequences are prepared in known fashion, such as described in the Weier et al. publication noted above. In addition to the DNA sequences of interest, which are sought to be amplified, a thermally stable enzyme, such as TAQ is included in the sample composition which is placed either in test tubes for subsequent positioning of the test tubes in the wells, or as pointed out above, placed directly into the wells of the cycling device. Thermally conductive liquid is then introduced into the cycling device, so that the samples to be amplified are heated and then cooled in repetitive, cyclic fashion. This cyclic heating and cooling allows amplification of the DNA sequences particularly due to the presence of the thermally stable DNA polymerase.

Figure 8:
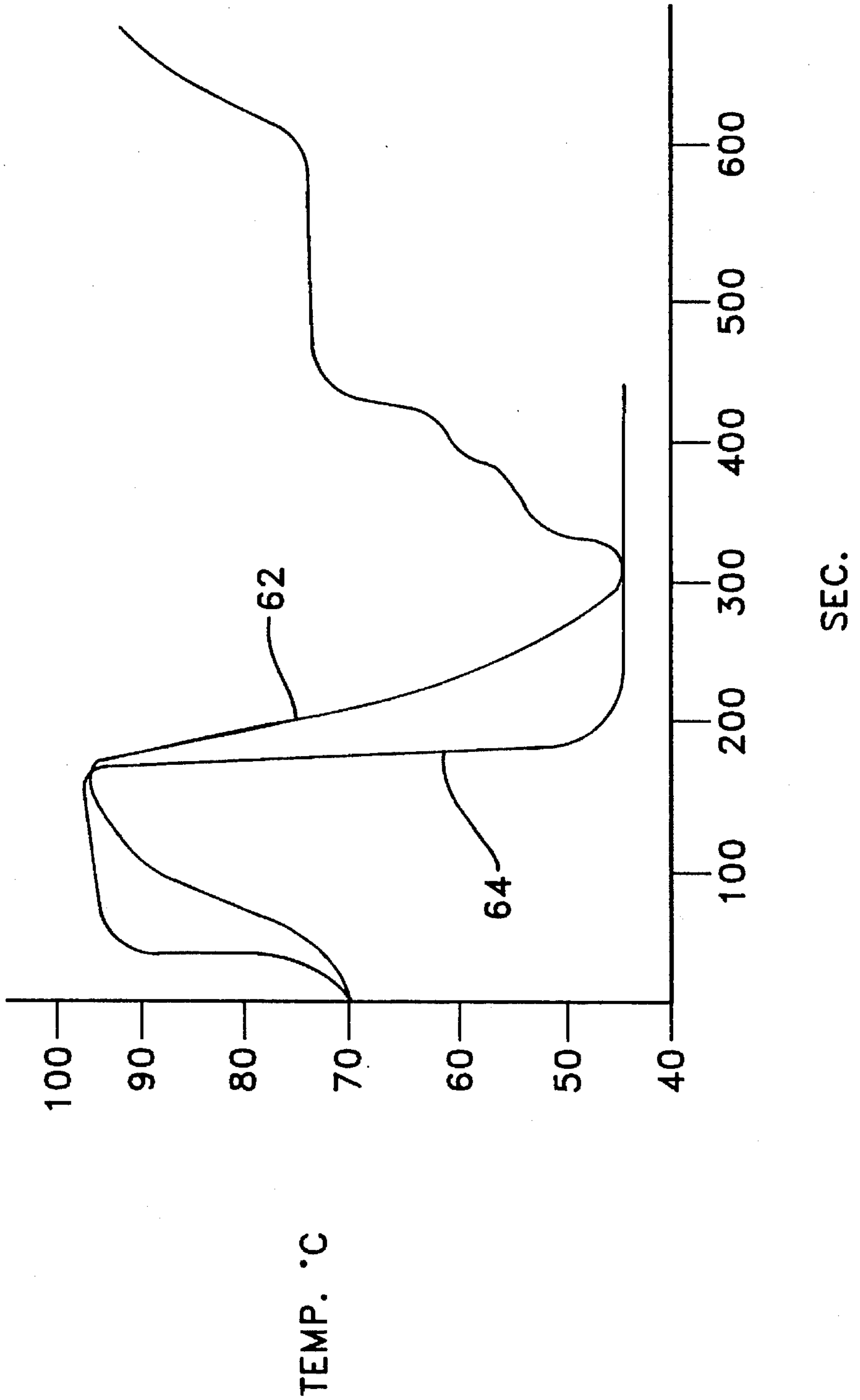
FIG. 8 is a graphic representation of the temperature profiles of samples of materials during polymerase chain reaction, comparing an existing thermal cycle apparatus with the rapid thermal cycle apparatus of the present invention.

FIG. 8 illustrates, in graphic form, the temperature profiles of samples of DNA segments undergoing amplification in the polymerase chain reaction procedure. The curve designated by numeral 62 is the profile achieved by Weier et al. using a thermal cycle apparatus as described in their publication. The profile, indicated by numeral 64, of a sample of DNA sequences during PCR using the rapid thermal cycle apparatus of the present invention, is substantially different. It can be seen that in both profiles 62 and 64, the sample reaches a temperature of approximately 95° C. on the hot cycle, and then rapidly cools down to about 44° C. on the cold cycle, before the cycles were repeated. However, it can be seen that profile 64, which results from using the rapid thermal cycle apparatus of the present invention has a substantially more rapid rate of increase of temperature of the hot cycle, as well as a substantially more rapid decrease of temperature on the cold cycle. Indeed, it can be calculated that profile 64 is between four and five times as fast on the heat cycle as profile 62, which uses existing cycle apparatuses. With respect to the cold cycle, use of the present rapid thermal cycle apparatus produces temperature changes between three and four times as fast on the cooling cycle as the existing cycle apparatuses. As a result of use of the present invention, it is possible to realize temperature changes in the DNA sample of at least 1.0° C./sec, and even higher.

Accordingly, the present invention provides an apparatus and method for thermally cycling samples of materials between lower and higher temperatures which cycles substantially faster, in the hot and cold cycles, then presently known and used cycling apparatuses, employed in PCR and other amplification procedures. Substantial efficiencies are achieved with the present invention, resulting in a lower cost unit, both for material costs and costs of operation.

What is claimed is:

1. A thermal cycle apparatus useful for the amplification of nucleic acid sequences comprising:

a body having a hollow interior comprising an upper surface connected by first and second sidewalls and first and second endwalls to a lower surface wherein said sidewalls and said endwalls have a thickness of about 0.002 to about 0.125 inches (from about 0.051 to about 3.175 mm) and said body comprising a low thermal mass material selected from plastic or ceramic;

a plurality of wells integrally formed with said upper surface of said body depending downwardly into said hollow interior;

a first liquid passage port integrally formed with said first endwall;

a second liquid passage port integrally formed with said second endwall;

a first valve for directing fluid flow to and from said first liquid passage port; a second valve for directing fluid flow to and from said second liquid passage port;

a first liquid tank and a first piston downstream from said first valve whereby a forward stroke of said first piston forces liquid from said first liquid tank through said first valve and onward into said body and a rearward stroke of said first piston forces liquid from said body through said first valve and onward into said first liquid tank; and a second liquid tank and a second piston downstream from said second valve whereby a forward stroke of said second piston forces liquid from said second liquid tank through said second valve and onward into said body and a rearward stroke of said second piston forces liquid from said body through said second valve and onward into said second liquid tank.

* * * * *